United States Patent
Beuhler et al.

[11] Patent Number: 5,917,966
[45] Date of Patent: Jun. 29, 1999

[54] INTERFEROMETRIC OPTICAL CHEMICAL SENSOR

[75] Inventors: Allyson Beuhler, Downers Grove; Anthony J. Polak, Lake Zurich, both of Ill.

[73] Assignee: Motorola Inc., Schaumburg, Ill.

[21] Appl. No.: 08/572,827

[22] Filed: Dec. 14, 1995

[51] Int. Cl.$^6$ ........................................... G02B 6/00
[52] U.S. Cl. ........................ 385/12; 250/227.23; 356/432
[58] Field of Search ................ 385/12, 147; 250/423 R, 250/425, 227, 227.23, 226; 73/23.2, 23.1, 31.06; 359/507; 356/432; 422/86, 88, 91

[56] References Cited

U.S. PATENT DOCUMENTS

| | | | |
|---|---|---|---|
| 3,989,938 | 11/1976 | Auth | 235/151.35 |
| 4,417,815 | 11/1983 | Murray et al. | 356/349 |
| 4,661,320 | 4/1987 | Ito et al. | 250/227.23 |
| 4,872,759 | 10/1989 | Stich-Baumeister et al. | 356/432 |
| 4,936,645 | 6/1990 | Yoon et al. | 385/12 |
| 4,969,742 | 11/1990 | Falk et al. | 385/12 |
| 5,021,731 | 6/1991 | Saaski et al. | 324/96 |
| 5,262,842 | 11/1993 | Gauglitz et al. | 385/12 |
| 5,314,828 | 5/1994 | Dalla Betta et al. | 436/118 |
| 5,322,798 | 6/1994 | Sadowski | 436/113 |
| 5,338,515 | 8/1994 | Dalla Betta et al. | 422/95 |
| 5,377,008 | 12/1994 | Ridgway et al. | 356/361 |
| 5,405,583 | 4/1995 | Goswami et al. | 422/86 |

OTHER PUBLICATIONS

"Thermo–Optic Waveguide Interferometric Modular/Switch in Glass" by Haruna et al., iEE Proceddings, vol. 131. PT.H, No. 5, Oct. 1984, (pp. 322–324), Jun. 1984.

S.R. Kidd, J. S. Barton, M. N. Inci and J.D. Jones Unsteady Gas Temperature Measurement Using an Altra–Short Optical Fibre Fabry–Perot Interferometer, Physics Dept., Heriot–Watt University, Edinburgh, UK, Mar. 21, 1994.

M. Huruna, Prof. J. Koyama Thermo–optic Waveguide Interferometric Modulator/Switch in Glass, Dept. of Electronics, Faculty of Engineering, Osaka University, Osaka, Japan, Jun. 7, 1984.

U. Fischer, T. Zinke, B. Schuppert and K. Petermann, Singlemode Optical Switches Based on SOI Waveguides with Large Cross–Section, Electronics Letters, Mar. 3, 1995, vol. 30, No. 5.

*Primary Examiner*—Akm E. Ullah
*Attorney, Agent, or Firm*—Nicholas C. Hopman

[57] ABSTRACT

An optical sensor (100) that measures gas concentration (121) includes a light input port (103), and a light output port (111). A reference waveguide (105) and a measurement waveguide (113) are both coupled between the light input port (103) and the light output port (111). The measurement waveguide (113) preferably includes a hydrocarbon-catalytic material (114). When light (101) is injected into the light input port (103), the light traverses to the light output port (111) via both waveguides (105,113). Preferably, the hydrocarbon-catalytic material (114) in the measurement waveguide (113) will react with certain hydrocarbons present in an engine's exhaust gas stream (121) and heat will be generated in the measurement waveguide (113). This heat generation will change a refractive index and optical path length of the measurement waveguide (113) compared to the reference waveguide (105). A detector (117) detects light present at the light output port (111) which will have an intensity dependent on a difference between the refractive index and optical path length of the measurement waveguide (113) and the reference waveguide (105).

8 Claims, 1 Drawing Sheet

INTERFEROMETRIC OPTICAL CHEMICAL SENSOR

FIELD OF THE INVENTION

This invention is generally directed to the field of sensors, and specifically for a sensor for measuring gas concentrations. This approach can be useful for determining concentrations of various gases in an internal combustion engine's exhaust gas stream.

BACKGROUND OF THE INVENTION

Optical chemical sensors can be applied to determine concentrations of certain gases. One application is for measuring concentrations of various gases in an internal combustion engine's exhaust gas stream. One reason to do this is that environmentally driven emissions legislation is regularly being changed to require lower and lower emissions of pollutants from vehicles. In particular, The California Air Resources Board (CARB) is leading an effort with their OBDII (On-Board Diagnostics II) requirement. OBDII requires detection of emitted hydrocarbons in the 100 PPM (parts per million) range.

There are many design challenges to achieve a robust sensor that can measure hydrocarbon emissions while surviving an extreme environment found in vehicular applications. This sensor must not only achieve a sensitivity required to measure hydrocarbons in the 100 PPM range, but also operate in an exhaust gas temperature that can range from 400° C. to over 1,000° C., have a resolution of ±50 PPM, survive extreme levels of vibration, survive in an acid environment on an automotive exhaust system, and operate while exposed to significant electromagnetic interference (EMI).

Contemporary electrical-circuit based hydrocarbon sensors include a hydrocarbon sensor based on a wire that has a catalyst impregnated bead of ceramic disposed on it. When the wire is exposed to a hydrocarbon, the catalyst burns the hydrocarbon, the wire gets hot, and the resistance of the wire changes. This scheme is not sensitive enough or robust enough to vibration, and furthermore has poor repeatability.

Other electrical-circuit based hydrocarbon sensors include silicon based sensors. These silicon based sensors cannot operate at the elevated temperatures of the exhaust gas stream and therefore apply complex cooling means to maintain a relatively low temperature at the sensor so that it will survive. Being electrical-circuit based these sensors are also susceptible to mechanical failure of electrical interconnections due to vibration, and also to EMI exposure.

One prior art optical scheme absorbs hydrocarbons into a chemically selective cladding disposed in a core structure. When exposed to light the presence of the hydrocarbons causes some of the light in the core to be absorbed in the cladding layer. A sensed reduction in light output is then used as a measure of hydrocarbon concentration. This scheme lacks sufficient selectivity, and speed of response.

What is needed is an improved hydrocarbon sensor that operate in the extreme temperature range of an automotive exhaust gas system, have a resolution of ±50 PPM, survive extreme levels of vibration, survive in an acid environment on an automotive exhaust system, and operate while exposed to significant electromagnetic interference (EMI).

DETAILED DESCRIPTION OF A PREFERRED EMBODIMENT

Figure 1:
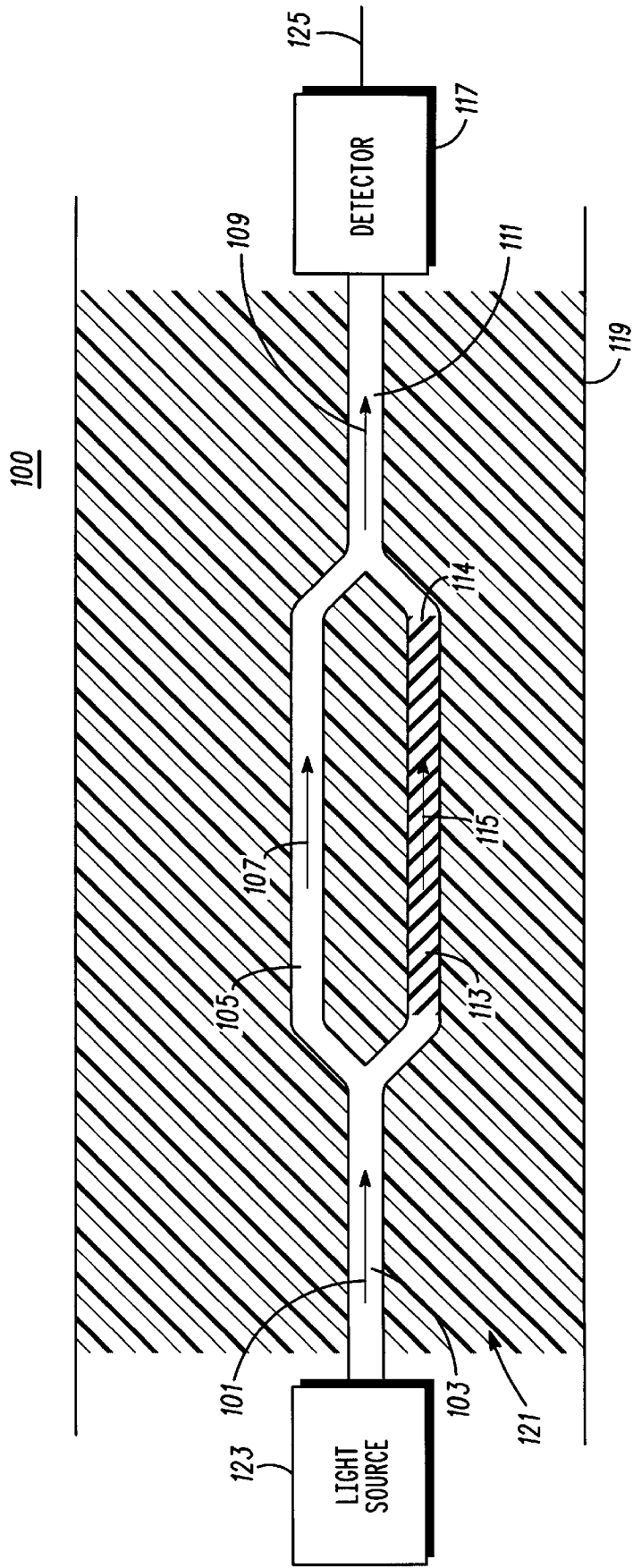
FIG. 1 is a cross section of an optical sensor in accordance with a preferred embodiment of the invention.

An interferometric optical sensor, preferably for measuring hydrocarbon content in an internal combustion engine exhaust gas stream, is constructed in a Mach-Zehnder configuration. A reference waveguide and a measurement waveguide are both coupled between the light input port and the light output port. The measurement waveguide includes a hydrocarbon-catalytic material. When light is injected into the light input port, the light traverses to the light output port via both waveguides. The hydrocarbon-catalytic material in the measurement waveguide will react with certain hydrocarbons present in the engine's exhaust gas stream and heat will be generated in the measurement waveguide. This heat generation will change both the refractive index of the measurement waveguide and its length compared to the reference waveguide. A detector detects light present at the light output port which will have an intensity dependent on the difference between the refractive index (and path length difference) of the measurement waveguide and the reference waveguide. Preferably, to meet the aforementioned CARB OBDII emissions standards, the sensor will be configured to sense non-methane hydrocarbon content in an automotive exhaust gas stream.

More specifically, an optical architecture hydrocarbon sensor is configured using a Mach-Zehnder interferometer. One path of the interferometer is used as a reference path, or branch, and another path, or branch, of the interferometer is doped with a hydrocarbon-catalytic—preferably a platinum electrode. Optionally, any Group VIII metal, or its alloy can be used. Group VIII elements comprise Fe, Ru, Os, Co, Rh, Ir, Ni, Pd, and Pt. When exposed to hydrocarbons in an exhaust gas stream (in the presence of oxygen) the platinum electrode generates heat. This heating effect changes the optical path length and the index of refraction of the waveguide of the interferometer. When a light source is input into the interferometer a phase change occurs in the platinum doped path compared to the reference path and a measured change in the intensity of the light at the output side of the interferometer is observed when the two light beams are combined. The magnitude of this change being indicative of the phase shift in the platinum doped path compared to the reference path, and related to the hydrocarbon concentration. A more thorough understanding of the preferred embodiment can be appreciated by viewing FIG. 1.

In FIG. 1, a sensor 100 is positioned within an exhaust plenum 119 of an internal combustion engine. The exhaust plenum 119 carries a stream on exhaust gas 121. The sensor 100 is excited by a light source 123 which generates light wave 101. The light wave 101 is injected into a light input port 103 of the sensor 100. A reference path waveguide 105 conducts a portion,107, of the injected light 101. A measurement path waveguide 113 conducts another portion 115 of the injected light 101. At a light output port 111 the lightwaves 107 and 115 are combined into an interference pattern whose output intensity 109 is the summation of the lightwaves 107 and 115.

As mentioned earlier a platinum electrode 114 is disposed within the measurement path waveguide 113. As hydrocarbons react with the platinum electrode 114, the phase of the injected light 115 is changed because the refractive index of the measurement waveguide 113 and its length change dependent on the reaction. Light from the reference path, 107 of the injected light 101 and another portion (changed phase) light 115 is arithmetically summated in a detector 117. The detector provides a signal 125 indicative of the hydrocarbon content in the exhaust gas stream 121. Next, fabrication details of the sensor 100 will be discussed.

The sensor 100 is fabricated using glass waveguides positioned on a silicon, or a ceramic substrate. A catalyst reactive to hydrocarbons is deposited on one branch of the interferometer. For instance, the substrate material can be quartz, the waveguide layer can be silicon nitride, and the cladding can be $SiO_2$. Because of its optical architecture the sensor 100 is not susceptible to EMI (electromagnetic interference). This is a significant advantage over prior art electrical-circuit based sensors which can exhibit erratic and inaccurate behavior when subjected to the relatively high levels of EMI typical in the automotive environment. Also, since there are no physical electrical contacts the sensor 100 is not susceptible to failure via corrosion as are prior art electrical-circuit based sensors.

The waveguides 105, 113 are preferably constructed using a single-mode ($TE_0$) waveguide. By choosing this configuration multi-mode fibers can be used to construct a single-mode waveguide. A multi-mode fiber approach is preferred because alignment of the waveguides is not as critical as in the single-mode fiber approach.

The device's sensitivity is dependent on; the length of the waveguides 105, 113; the temperature differential between the waveguides 105, 113; the temperature coefficient of expansion of the waveguide material; and the temperature coefficient of the index of refraction of the waveguide material. Preferably, the waveguides 105, 113 are about 1 cm in length. This 1 cm length provides sufficient sensitivity to detect hydrocarbons at below the 100 PPM level.

There are several methods by which light can be coupled in and out of the waveguides. Prisms with an index of refraction greater than that of the waveguide and cladding layer can be used (for instance rutile for the $Si_3N_4$ waveguide described above). However, it is advantageous from a manufacturing and robustness point of view to couple light in and out of the device using features that can be incorporated into the substrate, waveguide or cladding layer, such as diffraction gratings or tapers.

It is oftentimes not practical to develop a catalyst that is selective to only one chemical compound or chemical species that are found in automotive exhaust gas streams. One approach to solve this problem is to measure different combinations of species and then use a subtractive scheme to derive the species of interest. For instance, an automotive exhaust gas stream contains hydrogen, and methane in addition to higher hydrocarbons. In general detection of methane may not be important in this application. However, many catalysts that are sensitive to higher hydrocarbons are also sensitive to methane. One approach to solve this problem is to use two sensors; one that is selective to only methane; and a second that is sensitive to all hydrocarbons. Then by subtracting output signals derived from both sensors a measure of the concentration of the non-methane hydrocarbon in the gas stream can be derived.

Advantages of the described approach include physical robustness due to the fact that there are no wirebonds to break, no bondpads to corrode, and no wires to break due to vibration. Because optical signals are being used EMI susceptibility is not an issues as it is with electrically based prior art schemes. By applying the described approach a more reliable sensor can be constructed compared to prior art schemes.

What is claimed is:

1. An optical sensor for measuring gas concentration comprising:

a light input port;

a light output port;

a reference waveguide coupled between the light input port and the light output port; and a measurement waveguide coupled between the light input port and the light output port, the measurement waveguide having a catalytic material disposed thereon.

2. A sensor in accordance with claim 1 wherein the catalytic material comprises a hydrocarbon-catalytic material.

3. A sensor in accordance with claim 2 wherein the hydrocarbon-catalytic material comprises any Group VIII metals and its alloys.

4. A sensor in accordance with claim 2 wherein the hydrocarbon-catalytic material comprises platinum.

5. A sensor in accordance with claim 1 further comprising:

a light source for outputting light energy to the light input port; and a detector for measuring a light energy emitted from the light output port, and for providing a signal indicative of the hydrocarbon content in the exhaust gas stream dependent thereon.

6. An optical sensor disposed in an internal combustion engine exhaust gas stream for measuring hydrocarbon content of the exhaust gas stream comprising:

a light source for outputting light energy;

an optical waveguide comprising an light input port for receiving the light energy outputted from the light source, a light output port, a reference path coupled between the light input port and the light output port, and a measurement path coupled between the light input port and the light output port, wherein the measurement path is treated with a material acting as a catalyst when exposed to hydrocarbons in the exhaust gas stream; and a detector for measuring a light energy emitted from the light output port, and for providing a signal indicative of the hydrocarbon content in the exhaust gas stream dependent thereon.

7. A sensor in accordance with claim 6 wherein the material acting as a catalyst comprises any Group VIII metals and its alloys.

8. A sensor in accordance with claim 6 wherein the material acting as a catalyst comprises platinum.

* * * * *